United States Patent [19]

Arlt et al.

[11] Patent Number: 6,072,052
[45] Date of Patent: Jun. 6, 2000

[54] METHOD FOR THE PRODUCTION OF IVERMECTIN

[75] Inventors: Dieter Arlt, Lemgo; Gerhard Bonse, Köln, both of Germany

[73] Assignee: Bayer Aktiengesellschaft, Leverkusen, Germany

[21] Appl. No.: 09/297,241

[22] PCT Filed: Oct. 20, 1997

[86] PCT No.: PCT/EP97/05777

§ 371 Date: Apr. 27, 1999

§ 102(e) Date: Apr. 27, 1999

[87] PCT Pub. No.: WO98/18806

PCT Pub. Date: May 7, 1998

[30] Foreign Application Priority Data

Oct. 31, 1996 [DE] Germany .......................... 196 44 050

[51] Int. Cl.[7] .......................... C07H 17/08; C07H 19/01
[52] U.S. Cl. .............................................. 536/124; 536/7.1
[58] Field of Search ....................................... 536/7.1, 124

[56] References Cited

U.S. PATENT DOCUMENTS 5,656,748  8/1997  Arlt et al. ................................ 536/124

FOREIGN PATENT DOCUMENTS

| 0 086 040 | 6/1987 | European Pat. Off. . |
| 0 086 046 | 6/1987 | European Pat. Off. . |
| 0 283 615 | 5/1991 | European Pat. Off. . |
| 0 729 971 A1 | 9/1996 | European Pat. Off. . |
| 195 07 018 A1 | 9/1996 | Germany . |
| 98/18806 | 5/1998 | WIPO . |
| 98/38201 | 9/1998 | WIPO . |

*Primary Examiner*—Howard C. Lee
*Attorney, Agent, or Firm*—Joseph C. Gil; Godfried R. Akorli

[57] ABSTRACT

The present invention relates to a process for preparing ivermectin by selective hydrogenation of avermectin and subsequent removal of the catalyst.

1 Claim, No Drawings

METHOD FOR THE PRODUCTION OF IVERMECTIN

The present invention relates to a process for preparing ivermectin by selective hydrogenation of avermectin and subsequent removal of the catalyst.

Ivermectin is a known compound which has excellent biological activities and which is widely used as an anthelmintic, ectoparasiticide, insecticide and acaricide.

It is known (EP-A 0 001 689) to prepare ivermectin by selective catalytic hydrogenation from avermectin $B_{1a}$ and $B_{1b}$. Avermectin is produced by biotechnological methods with the aid of *Streptomyces avermitilis*. It has five double bonds. To prepare ivermectin from this starting material, a selective catalyst is required which only hydrogenates the 22,23-double bond.

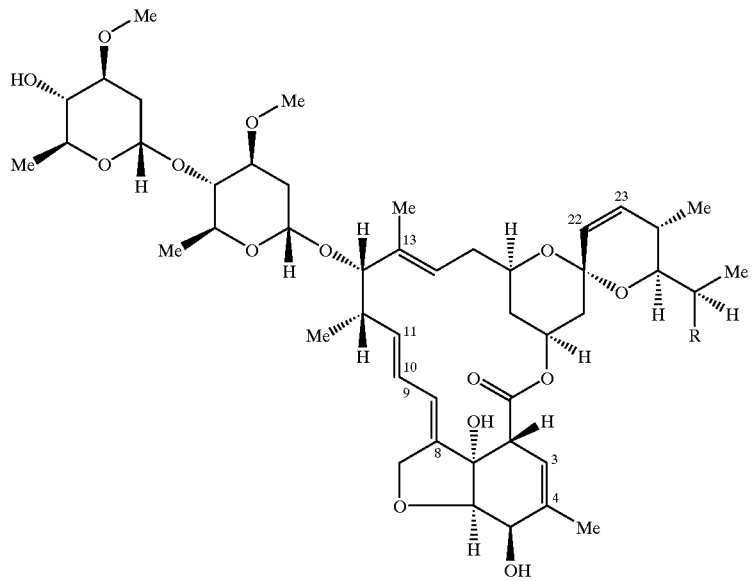

Avermectin $B_{1a}$ (R: -ethyl)
Avermectin $B_{1b}$ (R: -methyl)

From EP-A 0 001 680, it is known to use catalysts of the general formula $[(R)_3P]_3RhX$ for this purpose, and Wilkinson's catalyst $[Ph_3P]_3RhCl$ is preferably employed. Relatively large amounts of this catalyst (0.05 to 0.5 mol/mol of avermectin) are employed here to achieve the desired hydrogenation.

After the hydrogenation, it is necessary to remove the noble metal as completely as possible from the product to obtain the active compound in a form which conforms to the specifications (heavy metal content<10 ppm).

For this reason, and because of the high cost of rhodium, it has been proposed (EP-A 0 059 616) to use a special recovery process for removing and recycling the considerable amounts of this noble metal which have to be used in the preparation of ivermectin.

This process, which is described in EP-A 59 616, comprises the treatment of the product solutions which are obtained after the hydrogenation with certain organic sulphur compounds at elevated temperatures, for example 95° C., for several hours, followed by cooling the resulting mixture to from 0 to 5° C. and then by filtration of the precipitated rhodium compounds and, if appropriate, extraction of the filtered organic crude solution with aqueous sodium carbonate solution for further purification.

The removal of the catalyst metal in this manner is both time- and energy-consuming, and in addition to this, the sensitive product is put under stress and the ligands (phosphines) which are contained in the catalyst remain in the product. In this procedure, the product is furthermore additionally contaminated by addition of an excess of organic sulphur compounds (5 mol/mol of rhodium). To prepare the pure active compound, these components have to be removed by recrystallization, which results in significant losses.

The present invention provides a process for preparing ivermectin which permits simple removal both of the rhodium employed and of the organic components of the catalyst system from the product solution which is obtained after the hydrogenation to give an active compound which can be processed with low loss of material to give a form suitable for use.

In this process, avermectin $B_{1a}$ and $B_{1b}$ is hydrogenated and both the catalyst metal and the organic components of the catalyst system are removed in a simple manner from the resulting reaction solutions.

In the process according to the invention, mixtures of avermectin $B_{1a}$ and $B_{1b}$ are reacted by selective hydrogenation using catalysts which are obtained in a manner known per se from rhodium salts or from complex rhodium compounds and phosphines, if appropriate by adding hydrazine or hydrazine salts, using complex-forming phosphines of the formula (I),

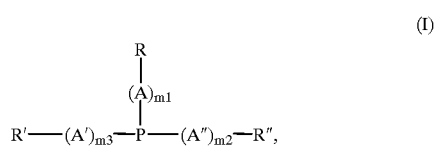

in which

R, R' and R" independently of one another each represent hydrogen, alkyl or optionally alkyl-, alkoxy-, halogen- or halogenalkyl-substituted arylalkyl, A, A' and A" independently of one another each represent optionally alkyl- or alkoxy- and/or optionally halogen- or halogenoalkyl-substituted divalent aromatic radicals, $m_1$, $m_2$ and $m_3$ are identical or different and are each 0 or 1, as phosphines, the sum of the carbon atoms present in the alkyl and alkoxy groups being at least 12, to give ivermectin, and the catalyst system is subsequently removed from the resulting reaction mixture, if appropriate after removal of the solvent, using lipophilic solvents.

The preparation processes for the catalysts are known (see, for example, Inorg. Synth. 10, 67 (1967) and EP-A 0 086 040, EP-A 0 283 615 and Tetrahedron Vol. 7, No. 19/20, p. 2087–2089 (1988)). The rhodium compounds suitable for use as starting materials for the preparation of the catalysts are known; rhodium salts which may be mentioned as examples are rhodium(III) chloride hydrate and rhodium (III) bromide hydrate, suitable precursors from the series of the rhodium complex compounds are, for example (1c,5c-cyclooctadien)rhodium(I) chloride dimer, (1,5-hexadiene) rhodium(I) chloride dimer and (2,5-norbornadiene)rhodium (I) chloride dimer, and also (1,5-cyclooctadiene)rhodium(I) acetylacetonate.

The phosphines of the formula (I) which are used according to the invention are known or can be prepared by known methods (see Houben-Weyl, Methoden der Organischen Chemie, 4th ed., vol. XII/1, Georg Thieme Verlag Stuttgart, 1963).

Preference is given to using phosphines of the formula (I) for the process according to the invention in which independently of one another R, R', R" represent hydrogen or $C_1$–$C_{20}$-alkyl or represent optionally $C_1$–$C_{20}$-alkyl-, $C_1$–$C_{20}$-alkoxy-, halogen-, in particular chlorine-, fluorine-, bromine-, 1-5-halogeno-$C_1$–$C_4$-alkyl-, in particular trifluoromethyl-substituted aryl-$C_1$–$C_4$-alkyl, in particular benzyl or phenylethyl, and in which independently of one another A, A', A" represent an optionally $C_1$–$C_{20}$-alkyl-, $C_1$–$C_{20}$-alkoxy-, halogen-, in particular fluorine- or chlorine-, 1-5-halogeno-$C_1$–$C_4$-alkyl-, in particular trifluoromethyl-substituted divalent aromatic radical, in particular phenyl, and in which $m_1$ and $m_2$ are 1 and $m_3$ is 0, the sum of the carbon atoms in the alkyl and alkoxy groups being at least 12, preferably at least 15 and particularly preferably at least 18.

Particular preference is given to phosphines of the formula (I) in which independently of one another R, R', R" represent hydrogen or $C_1$–$C_{20}$-alkyl or represent optionally $C_1$–$C_{20}$-alkyl-, $C_1$–$C_{20}$-alkoxy-, halogen-, in particular chlorine-, fluorine-, bromine-, 1-5-halogeno-$C_1$–$C_4$-alkyl-, in particular trifluoromethyl-substituted aryl-$C_1$–$C_4$-alkyl, in particular benzyl or phenylethyl, and in which independently of one another A, A', A" represent an optionally $C_1$–$C_{20}$-alkyl-, $C_1$–$C_{20}$-alkoxy-, halogen-, in particular fluorine- or chlorine-, 1-5-halogeno-$C_1$–$C_4$-alkyl-, in particular trifluoromethyl-substituted divalent aromatic radical, in particular phenyl, and in which $m_1$, $m_2$, $m_3$ represent 1, the sum of the carbon atoms in the alkyl and alkoxy groups being at least 12, preferably at least 15 and particularly preferably at least 18.

Examples which may be mentioned are:

(2-dodecyl-phenyl)-diphenyl-phosphine, (3-dodecylphenyl)-diphenyl-phosphine, (4-dodecylphenyl)-diphenyl-phosphine, bis-(4-tert-butylphenyl)-(4-dodecyl)-phosphine, tris-(4-tert-butylphenyl)-phosphine, bis-o-tolyl-(4-dodecylphenyl)-phosphine, (4-octadecylphenyl)-diphenyl-phosphine, dodecyl-diphenyl-phosphine, bis-(dodecyl)-phenyl-phosphine, methyl-bis-(dodecylphenyl)-phosphine, (4-trifluoromethylphenyl)-bis-(dodecyl)-phenyl-phosphine, (4-octadecylphenyl)-bis-(4-chlorophenyl)-phosphine, bis-(2-methoxyphenyl)-(4-dodecylphenyl)-phosphine, (4-dodecyloxyphenyl)-diphenyl-phosphine, dodecylbenzyl-diphenyl-phosphine, 4-biphenyl-bis-(dodecylphenyl)-phosphine, tris-(octylphenyl)-phosphine, tris-(hexylphenyl)-phosphine, tris-(nonylphenyl)-phosphine, tris-(decylphenyl)-phosphine, bis-(hexadecylphenyl)-phenyl-phosphine, bis (octadecylphenyl)-phenyl-phosphine.

After the preparation, the catalysts can be isolated and employed in pure form for the hydrogenation. However, it is also possible and particularly advantageous to synthesize the catalysts in situ and to use the solutions obtained in this manner for the selective hydrogenation. It may be advantageous to add an excess of the phosphine used as ligand to the hydrogenation batch.

Rhodium salts and phosphines of the formula (I) are employed in a molar ratio of from 1:1 to 1:20, preferably from 1:1 to 1:15, particularly preferably from 1:3 to 1:15, to prepare the catalyst system (cf. in particular EP-A 0 086 046). If appropriate, hydrazine or derivatives thereof are added in a molar ratio of from 1:1 to 1:10, based on the rhodium salt.

Per mole of substrate, the amount of additional phosphine of the formula (I) which is added in the process according to the invention is in an order of magnitude of from 0.01 to 0.06 mol (cf. EP-A 086 046). However, it is easily possible to determine the most favourable amount by a test series.

The catalytic hydrogenation is carried out in customary solvents, such as, for example, alcohols, aromatic hydrocarbons, in ethers, ketones, esters or in mixtures of solvents, for example in methanol/hydrocarbon or acetone/hydrocarbon mixtures.

The temperature during the hydrogenation is in the range of from about 40 to 100° C., the hydrogen pressure is in the range from approximately 1 to 50 bar. To shorten the reaction time, it is advantageous to operate under superatmospheric pressure, and a range of from 3 to 20 bar is preferred.

Owing to the lipophilic properties of the phosphines which are employed as catalyst ligand according to the invention, it is possible to remove the catalyst system from the product in a simple manner by extraction using suitable lipophilic solvents in which the process product (ivermectin) is only soluble to a small extent, if at all.

Thus it is possible, for example, to remove, after the hydrogenation, the solvent by vacuum distillation and subsequently from the remaining product/catalyst mixture the catalyst system (metal complex and phosphine) by extraction with lipophilic solvents. The resulting ivermectin is essentially free of catalyst metal and ligand phosphine and can be obtained in high purity, for example, by a subsequent recrystallization which is known per se and which serves to remove small amounts of by-products. It is also possible to purify the product further, after removal of the catalyst system, by chromatography, virtually without losses.

Suitable for the selective removal of the catalyst system are lipophilic solvents, such as, for example, aliphatic hydrocarbons—cyclohexane, methylcyclohexane, isooctane, petroleum ether, cleaner's naphtha or ethers having larger hydrocarbon radicals, such as, for example, tert-octyl methyl ether, may be mentioned by way of example.

A variant of removing the catalyst system after the hydrogenation consists in adding the selective lipophilic solvent to the product/catalyst solution which is obtained after the selective hydrogenation, and distillatively removing the polar solvent component which is present in the hydrogenation batch. This results in unmixing, the ivermectin precipitates out and can be separated from the solution containing the catalyst system by decanting or filtration.

A further variant for removing the catalyst system after the hydrogenation step comprises the subsequent preparation of a two-phase mixture which permits separation of the ivermectin from the catalyst system (catalyst complex and excess phosphine). To this end, the solvent used for the hydrogenation step is, if required, removed by distillation, advantageously under reduced pressure to protect the product mixture, and is replaced by a solvent mixture which is suitable for the separation.

Solvent mixtures which are suitable for this variant of the separation comprise a lipophilic component (see above) and polar solvents which are water-miscible, and water. Suitable polar components for such solvent mixtures are, for example, methanol, ethanol, acetone, butanone, acetonitrile, tetrahydrofuran, formamide, dimethylformamide and N-methylpyrrolidone. Depending on the choice of components, the water content of such solvent mixtures can vary; in general, it is from 5 to 60%, preferably 10 to 40%.

It has been found that, when such a two-phase system is mixed with the crude product of the hydrogenation step, the ivermectin is enriched predominantly in the polar component and the catalyst system predominantly in the lipophilic component. In this embodiment, it is advantageous to remove the catalyst system from the product in a continuous countercurrent process using an extraction column.

A further embodiment of the process according to the invention consists in using solvents or solvent mixtures which dissolve starting materials and product and also the catalyst system at an elevated temperature which corresponds to the hydrogenation conditions, and from which subsequently, after sufficient cooling, the desired product (ivermectin) precipitates, but in which the metal complex catalyst and the ligand phoshine remain dissolved even at lower temperature. In this case, the process product, essentially freed from the catalyst, can be separated from the remainder of the solution by filtration, while the catalyst metal is obtained in a simple manner in the distillation residue when the remainder of the solution is worked up by distillation, and it is then recycled.

Such solvents have amphiphilic properties and have both a lipophilic moiety and polar groupings. Examples which may be mentioned are isooctanol, dodecanol, methyl tert-octyl ether, mixtures of tert-butanol and isooctane and also tert-butyl methyl ether and isooctane.

It is very surprising that the catalysts or catalyst systems employed according to the invention make it possible both to hydrogenate avermectins to ivermectins with excellent selectivity and to separate in a simple manner product and catalyst system.

EXAMPLES

Example 1

A) Preparation of the Catalyst

Under an atmosphere of argon, a mixture of 7.5 mg of rhodium trichloride, 30.0 mg of tris-(hexylphenyl)-phosphine, 3 ml of acetone and 15 μl of hydrazine hydrate is heated with stirring and reflux cooling for 4 hours.

B) Hydrogenation

The catalyst solution obtained according to (A) is added to a solution of 4.3 g of avermectin ($B_{1a}$ and $B_{1b}$ mixture) in 25 ml of a mixture of acetone and cyclohexane in a ratio of 2:1. After addition of 51.4 mg of tris-(mexylphenyl) phosphine, the hydrogenation is carried out in a steel autoclave at a hydrogen pressure 5 bar and at 88° C. After a hydrogenation time of 4 hours, HPLC analysis shows a content of 8.9% of starting material, 89.9% of ivermectin ($B_{1a}$ and $B_{1b}$ mixture), tetrahydroavermectin content <0.1%.

D) Removal of the Catalyst System

The crude product obtained according to (B) is, after distillative removal of the solvent mixture, dissolved in a mixture of 35 ml of methanol and 20 ml of water and this solution is extracted with 25 ml of cyclohexane in a separating funnel. The phases are separated and concentrated under reduced pressure. The extraction is repeated twice in the same manner.

| Result: | The crude product of the hydrogenation step contains | 690 ppm of Rh |
|---|---|---|
| | The resulting product contains | |
| | after the 1st extraction | 39 ppm of Rh |
| | after the 2nd extraction | 29 ppm of Rh |
| | after the 3rd extraction | 22 ppm of Rh |

The catalyst system (catalyst and phosphine) extracted from the product contains 6332 ppm of Rh.

Example 2

A) Preparation of the Catalyst

Under an atmosphere of argon, a mixture of 7.5 mg of rhodium trichloride hydrate, 45.6 mg of tris-(octylphenyl)-phosphine (94% pure), 3 ml of acetone and 15 μl of hydrazine hydrate is heated with stirring and reflux cooling for 4 hours.

B) Hydrogenation 4.3 g of avermectin ($B_{1a}$ and $B_{1b}$ mixture) are, after addition of 53.2 mg of tris-(octylphenyl)-phosphine, hydrogenated using the conditions given in Example 1 (B). After a hydrogenation time of 7 hours, a crude ivermectin product is obtained which, according to HPLC analysis, contains 1.3% of avermectin, 94.8% of ivermectin and 2% of tetrahydroavermectin.

C) Removal of the Catalyst System

The resulting product is treated using the method of Example 1 (C). After the third extraction, a product is obtained which has a rhodium content of 9 ppm.

What is claimed is:

1. A process for preparing ivermectin, characterized in that mixtures of avermectin $B_{1a}$ and $B_{1b}$ are reacted by selective hydrogenation with a catalyst in a reaction solvent wherein the catalyst is selected from the group consisting of rhodium salts and rhodium-phosphine complexes wherein said catalyst is optionally derivatized with hydrazine or a hydrazine salt and the phosphine is defined by formula (I)

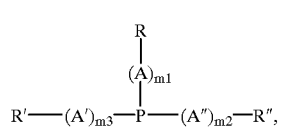

in which

R, R' and R" independently of one another each represent hydrogen, alkyl or optionally alkyl-, alkoxy-, halogen- or halogenalkyl-substituted arylalkyl, A, A' and A" independently of one another each represent optionally alkyl- or alkoxy- and/or optionally halogen- or halogenoalkyl-substituted divalent aromatic radicals, $m_1$, $m_2$ and $m_3$ are identical or different and are each 0 or 1, the sum of the carbon atoms present in the alkyl and alkoxy groups being at least 12, to give ivermectin, and the catalyst system is subsequently removed from the resulting recation mixture by extraction with a lipophilic solvent wherein the extraction step is optionally performed after the removal of the reaction solvent.

* * * * *